(12) United States Patent
Lee et al.

(10) Patent No.: US 7,772,441 B1
(45) Date of Patent: Aug. 10, 2010

(54) PROCESS FOR PRODUCING 3,4' DIHYDROXYBENZOPHENONE

(75) Inventors: Kiu-Seung Lee, Midlothian, VA (US); Michael Francis Vincent, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/393,310

(22) Filed: Feb. 26, 2009

(51) Int. Cl.
*C07C 45/00* (2006.01)

(52) U.S. Cl. ...................... 568/319; 568/332

(58) Field of Classification Search ................ 568/319, 568/332
See application file for complete search history.

(56) References Cited

U.S. PATENT DOCUMENTS

| | | | |
|---|---|---|---|
| 4,245,082 A | 1/1981 | Irwin | |
| 4,269,965 A | 5/1981 | Irwin | |
| 4,500,699 A | 2/1985 | Irwin et al. | |
| 4,617,369 A | * 10/1986 | Huynh-Ba | .................. 528/128 |

* cited by examiner

*Primary Examiner*—Sikarl A Witherspoon

(57) ABSTRACT

A process for synthesizing 3,4'dihydroxybenzophenone by reacting meta-hydroxybenzoic acid and phenol in the presence of a Lewis acid, and a protonic acid. Upon completion of the reaction the Lewis and protonic acids are removed and then the reaction product of 3,4'dihydroxybenzophenone is contacted with water (at temperature not greater than 10° C.) and ammonium hydroxide followed by filtration.

9 Claims, No Drawings

PROCESS FOR PRODUCING 3,4' DIHYDROXYBENZOPHENONE

BACKGROUND OF INVENTION

1. Field of Invention

This invention is directed to a process for producing 3,4'dihydroxybenzophenone.

2. Description of the Related Art

Various processes are disclosed in the prior art for producing 3,4'dihydroxybenzophenone including U.S. Pat. No. 4,269,965 issued May 26, 1981, U.S. Pat. No. 4,245,082 issued Jan. 13, 1981, and U.S. Pat. No. 4,500,699 issued Feb. 19, 1985, all to Robert S. Irwin.

There is a need for an improved, efficient, and economical process for producing 3,4'dihydroxybenzophenone which is a useful intermediate for making 3,4 diacetoxybenzophene.

SUMMARY OF THE INVENTION

The present invention is directed a method for producing 3,4'dihydroxybenzophenone comprising in order:
(a) combining m-hydroxybenzoic acid, phenol, a protonic acid and a Lewis acid to form a mixture,
(b) heating an agitated mixture of step (a) to a temperature in a range of 27-33° C. and a pressure of at least 5 psig to form a reaction product of 3,4'dihydroxybenzophenone present as solids in a solution,
(c) removing at least a portion of the protonic acid and Lewis acid from the formed reaction product of 3,4'dihydroxybenzophenone,
(d) contacting the reaction product of step (c) with (i) water at a temperature not greater than 10° C. and (ii) ammonium hydroxide to obtain a pH in a range of 4.5 to 6;
(e) filtering a mixture of step (d) to separate 3,4'dihydroxybenzophenone solids.

A preferred protonic acid is hydrofluoric acid (hydrogen fluoride) and a preferred Lewis acid is boron triflouride.

DETAILED DESCRIPTION OF THE INVENTION

Synthesis of 3,4'dihydroxybenzophenone

An initial first step in formation of 3,4 dihydroxybenzophenone is to form a mixture of m-hydroxybenzoic acid, phenol, a protonic acid and a Lewis acid. (As employed herein formation of a "mixture" includes formation of a "solution".)

Preferably the m-hydroxybenzoic acid and phenol are present in equimolar amounts to form the 3,4'dihydroxybenzophenone. It is understood that either the m-hydroxybenzoic acid or phenol may be present in excess compared to the exact ratio needed. However in such case the excess reactant will be present as an impurity in the formed 3,4'dihydroxybenzophenone.

For purposes of explanation, equimolar amounts means that reactants are combined such that the same number of moles of reactants are combined together. Another way of expressing this is that a ratio of the number of moles of reacted meta-hydroxybenzoic acid divided by the number of moles of reacted phenol is equal to one.

Protonic acids, as employed herein, are acids that form positive hydrogen ions or oxonium ($H_3O^+$) ions in an aqueous solution. Suitable protonic acids include hydrofluoric acid (hydrogen fluoride), hydrochloric acid, sulphuric acid, and hydrobromic acid (hydrogen bromide). It is understood that mixtures of the acids can be used. A preferred protonic acid is hydrofluoric acid (hydrogen fluoride).

Examples of Lewis acids useful include aluminum chloride, iron(III) chloride, boron trifluoride, niobium pentachloride and lanthanide triflates such as ytterbium (III) triflate. Mixtures of the acid can also employed. A preferred Lewis acid is boron trifluoride.

An initial first step in formation of a mixture of m-hydroxybenzoic acid, phenol, a protonic acid and a Lewis acid is preferably in several segments. A first segment involves forming a solution of meta-hydroxybenzoic acid, phenol and a protonic acid. As previously set forth a preferred protonic acid is hydrofluoric acid. Preferably the protonic acid is present in an amount of a least two times the total weight of the meta-hydroxbenzoic acid and phenol.

In the preferred mode, a second segment involves a separate addition of the Lewis acid to the solution of meta-hydroxybenzoic acid, phenol and protonic acid. As previously set forth a preferred Lewis acid is boron trifluoride.

Typically the mixture of m-hydroxybenzoic acid, phenol, a protonic acid and a Lewis acid is present in a pressure vessel, commonly known as a pressure reactor. The mixture in the reactor is heated to a temperature in a range of 27 to 33° C. and the pressure is allowed to increase to at least 5 psig thereby forming a reaction product of 3,4'dihydroxybenzophenone. Preferably the contents of the pressure reactor are agitated during the reaction.

For purposes of illustration a time of heating employing elevated pressure is a minimum of 4 hours. Also preferably the reaction mixture is allowed to room temperature over a prolonged time period such as 16 hours.

After release of the elevated pressure in the reactor, protonic acid and the Lewis acid are removed from the reaction mixture. A conventional separation method such as rotary distillation is suitable employing reduced temperature and pressure.

The reaction mixture then is contacted with ice water to extract residual protonic and Lewis acids, water soluble reactants and water soluble byproducts from the reaction mixture followed by use of aqueous ammonium hydroxide to neutralize remaining residual acid and to elevate the pH of the reaction mixture to a range of 4.5 to 6.

The resulting reaction mixture present as an aqueous slurry resulting is then filtered to recover 3,4'dihydroxybenzophenone as a salmon colored solid. The resulting 3,4'dihydroxybenzophenone preferably is washed with water and with cold methanol at a temperature of less than 15° C. to remove any residual water soluble impurities.

Typically, the resulting 3,4'dihydroxybenzophenone is present in a yield based on weight of at least 70%, preferably 80%, and most preferably at least 87% based on equimolar quantities of meta-hydroxy benzoic acid and phenol. The final product of this synthesis and can be used without further purification. Optionally, the resulting 3,4'dihydroxybenzophenone can be dried before further use. The melting point for this product was found to be in the range of 200-201° C.

In the following examples, all parts and percentages are designed as parts by weight and all temperatures are listed in degrees Celsius unless otherwise stated.

Example 1

Preparation of 3,4'-dihydroxybenzophenone

A pressure reactor was charged with 44 g of m-hydroxybenzoic acid, 32 g of phenol and 200 g of anhydrous hydrogen fluoride. The vessel was charged with 36.7 g of boron trifluoride gas and heated to 30° C. for four hours. The reaction mixture was then continuously rocked overnight at ambient temperature. The pressure was bled off and excess hydrogen fluoride was distilled into a caustic scrubber. The vessel was opened and the contents poured into 1 liter of ice water. An aqueous ammonium hydroxide solution (28.0-30.0% $NH_3$ basis by weight) was added to neutralize the batch to a pH of 4.5-6 and the slurry was filtered and the cake was washed 3 times with water and once with ice-cold methanol. The wet filter cake was recovered and dried overnight in a vacuum oven at 80° C. A resulting hard, lumpy material was ground to give 51.5 g of 3,4'-dihydroxybenzophenone, as a salmon colored powder with mp of 200-201° C. Residual product in the methanol filtrate was concentrated and cooled in an ice bath to give a second crop of product. The material was dried in an oven and ground to give 8.5 g of a beige powder. The two crops were identical by NMR and combined to give 60.0 g (87.9% yield) of intermediate for further use.

Comparative Example 1

Preparation of 3,4'-dihydroxybenzophenone

A pressure reactor was charged with 44 g of m-hydroxybenzoic acid, 32 g of phenol and 200 g of anhydrous hydrogen fluoride. The vessel was pressured with boron trifluoride gas and heated to 30° C. for four hours. The pressure was bled off and the excess HF was distilled to a caustic scrubber. The vessel was opened and the contents were poured into aqueous $NaHCO_3$ solution. The slurry (about 2 gallons) was filtered and the cake was washed with water, 5% aqueous $NaHCO_3$ solution and finally with water for a second time. The wet filter cake was dried for about 2 days in a vacuum oven at 80° C. This resulted in 41.4 g of 3,4'-dihydroxybenzophenone (60.6% yield).

What is claimed is:

1. A method for producing 3,4'dihydroxybenzophenone comprising in order:
   (a) combining m-hydroxybenzoic acid, phenol, a protonic acid and a Lewis acid to form a mixture,
   (b) heating an agitated mixture of step (a) to a temperature in a range of 27-33° C. and a pressure of at least 5 psig to form a reaction product of 3,4'dihydroxybenzophenone present as solids in a solution,
   (c) removing at least a portion of the protonic acid and Lewis acid from the formed reaction product of 3,4'dihydroxybenzophenone,
   (d) contacting the reaction product of step (c) with (i) water at a temperature not greater than 10° C. and (ii) ammonium hydroxide to obtain a pH in a range of 4.5 to 6;
   (e) filtering a mixture of step (d) to separate 3,4'dihydroxybenzophenone solids.

2. The method of clam 1 wherein step (a) comprises
   (i) forming a solution of meta-hydrobenzoic acid, phenol and protonic acid,
   (ii) adding Lewis acid to the solution of step (i).

3. The method of claim 1 wherein the protonic acid is hydrogen fluoride, sulfuric acid or hydrobromic acid.

4. The method of claim 3 wherein the protonic acid is hydrogen fluoride.

5. The method of claim 1 wherein the weight of protonic acid is at least two times the total weight of meta-hydrobenzoic acid and phenol.

6. The method of claim 1 wherein the Lewis acid is aluminum chloride, iron (III) chloride, boron trifluoride, niobium pentachloride or lanthanide trifllate.

7. The method of claim 6 wherein the Lewis acid is boron trifluoride.

8. The method of claim 1 wherein the protonic acid is hydrogen flouride and the Lewis acid is boron triflouride.

9. The method according to claim 1 where the pressure of step (b) is at least 10 psig.

* * * * *